(12) United States Patent
Miyata (10) Patent No.: US 7,169,407 B1
(45) Date of Patent: *Jan. 30, 2007

(54) CARBONYL STRESS-DECREASING AGENT

(75) Inventor: Toshio Miyata, 102 Ekuseru Isehara, 16-25, Sakuradai 2-chome, Isehara-shi, Kanagawa (JP) 259-1132

(73) Assignees: Toshio Miyata, Kanagawa (JP); Kiyoshi Kurokawa, Tokyo (JP); Tokai University Educational System, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/089,789

(22) PCT Filed: Oct. 6, 2000

(86) PCT No.: PCT/JP00/06987

§ 371 (c)(1),
(2), (4) Date: Aug. 19, 2002

(87) PCT Pub. No.: WO01/24790

PCT Pub. Date: Apr. 12, 2001

(30) Foreign Application Priority Data

Oct. 6, 1999 (JP) ................................ 11/285735

(51) Int. Cl.
*A61L 15/18* (2006.01)
*A61L 15/22* (2006.01)
*A01N 47/44* (2006.01)

(52) U.S. Cl. ...................................... 424/443; 514/151
(58) Field of Classification Search ................ 424/400, 424/464, 682, 691, 724, 443; 514/770, 784, 514/960, 151
See application file for complete search history.

(56) References Cited

U.S. PATENT DOCUMENTS 4,028,402 A   6/1977  Fischer et al. ......... 260/501.14
5,928,916 A * 7/1999  Keogh ........................ 435/174
5,952,356 A * 9/1999  Ikeda et al. ................. 514/340
6,117,451 A * 9/2000  Kumar ........................ 424/465
6,559,188 B1* 5/2003  Gatlin et al. ................ 514/641

FOREIGN PATENT DOCUMENTS

| AU | 756847 B2 | 1/2003 |
| EP | 1 108 434 A1 | 8/1999 |
| WO | WO 00/10606 | 3/2000 |
| WO | WO 00/69466 | 11/2000 |

OTHER PUBLICATIONS

Solomon, T. W. G. Organic Chemistry, 5th edn. John Wiley & Sons, Inc.: New York, 1992, pp. 701-704.*
Miyata, T. et al. Kidney International, 1999, 55, pp. 389-399.*
Ruggiero-Lopez, D. et al. Biochem. Pharmacol. 1999, 58, pp. 1765-1773.*
Layton et al., "Factors Influencing the Immunogenicity of the Haptenic Drug Chlorhexidine in Mice Part I. Molecular Requirements for the Induction of igE and igG Anti-hapten Antibodies," *Molecular Immunology*, 24(2): 133-141, 1987.
Ruggiero-Lopez et al., "Reaction of Metformin with Dicarbonyl Compounds. Possible Implication in the Inhibition of Advanced Glycation End Product Formation," *Biochemical Pharmacology*, 58: 1766-1773, 1999.
Tanaka et al., "Inhibitroy Effect of Metformin on Formation of Advanced Glycation end Products," *Current Therapeutic Research*, 58 (10) 693-697, 1997.
Yasuda et al., "Carbonyl Stress. A New Development of Advanced Glybonyl End Products," *Gendai Igaku* 45(2): 363-368, (English Abstract) 1997.
Lin and Jin, "Basis of Medical Pharmacology," I:311-312, World Book Publishing Company, Beijing (1994) (English Translation).
Ruggiero et al., "Reaction of metformin with reduced sugars and dicarbonyl compounds", Diabetologia (Supp. 1), 40:A310 (1997).
Song G., et al., Shenyang Chemical Industry 1:43-5, 1996.
Song G., et al., Silk 12:51-4, 1996.

* cited by examiner

*Primary Examiner*—Johann R. Richter
*Assistant Examiner*—James Henry Alstrum-Acevedo
(74) *Attorney, Agent, or Firm*—DLA Piper US LLP (57) ABSTRACT

The present invention provides agents that decrease carbonyl stress comprising biguanides, such as metoformin. Through oral administration and such, the carbonyl stress-decreasing agents of the present invention are useful as drugs directly acting against carbonyl stress in vivo.

16 Claims, 9 Drawing Sheets

CARBONYL STRESS-DECREASING AGENT

TECHNICAL FIELD

The present invention relates to carbonyl stress-decreasing agents.

BACKGROUND ART

An enhanced state of in vivo carbonyl compound production by non-enzymatic biochemical reactions is called "carbonyl stress". Carbonyl compounds are considered to be involved in aging and adult diseases, such as diabetes mellitus, and arteriosclerosis, via the Maillard reaction. The Maillard reaction is a non-enzymatic glycation reaction between a reducing sugar, such as glucose, and amino acids or proteins. Maillard reported this reaction in 1912, focusing on a phenomenon of brown coloration arising upon heating a mixture consisting of amino acid and reducing sugar (Maillard, L. C., Compt. Rend. Soc. Biol., 72:599 (1912)). The Maillard reaction is involved in brown coloration, generation of aromatic components, taste and protein denaturation, and such, during heating or storage of foods. Therefore, this reaction has been mainly studied in the field of food chemistry.

However, in 1968, glycated hemoglobin (HbAlc), a micro fraction of hemoglobin, was identified in vivo, and was further demonstrated to increase in patients with diabetes (Rahbar. S., Clin. Chim. Acta, 22: 296 (1968)). These findings brought attention to the significance of in vivo Maillard reactions, and the relationship between the reaction, the onset of adult diseases, such as diabetic complications and arteriosclerosis, and the progress of aging. For example, pyrraline and pentosidine, the late-stage products formed at post-Amadori compound formation reaction stages (advanced glycation end products; hereinafter abbreviated as AGE), are considered to serve as indices of aging and diabetes mellitus. In fact, highly reactive carbonyl compounds and AGE are accumulated at very high levels in blood and tissues of chronic renal failure patients, regardless of the presence or absence of hyperglycemia (Miyata, T. et al., Kidney Int., 51:1170–1181, 1997; Miyata, T. et al., J. Am. Soc. Nephrol., 7:1198–1206, 1996; Miyata, T. et al., Kidney Int. 55:389–399, 1999; Miyata, T. et al., J. Am. Soc. Nephrol. 9:2349–2356, 1998). This accumulation is ascribed to carbonyl stress in renal failure, which modifies proteins as a result of Maillard reaction with carbonyl compounds derived from sugars and lipids with amino groups (Miyata, T. et al., Kidney Int. 55:389–399, (1999)).

Thus, improving the carbonyl stress state by removing carbonyl compounds, which are generated in vivo, can result in the suppression of AGE formation associated with renal failure and thereby reduce tissue damages.

In peritoneal dialysis, waste products are excreted from blood across the peritoneum to the peritoneal dialysate. A peritoneal dialysate with high osmotic pressure (containing glucose, icodextrin, amino acids, and so on) delivers highly reactive carbonyl compounds accumulated in blood of renal failure patients across the peritoneum into the peritoneal dialysate in peritoneal cavity. This results in an increase in carbonyl compound concentration within the peritoneal dialysate to cause a carbonyl stress state. As a result, the peritoneal function is lowered, due to the modification of intraperitoneal proteins with carbonyl; this reaction, in turn, is presumed to be involved in the impairment of water-removing ability and ingravescence of peritoneal sclerosis (Miyata, T. et al., Kidney Int., 58:425–435, 2000; Inagi R., et al., FEBS Lett., 463:260–264, 1999; Ueda, Y., et al., Kidney Int. (in press); Combet, S., et al., J. Am. Soc. Nephrol., 11:717–728, 2000).

Indeed, the intraperitoneal carbonyl stress state induced by the introduction of glucose in peritoneal dialysis patients was demonstrated by immunohistochemical examination of the endothelia and mesothelia (Yamada, K. et al., Clin. Nephrol., 42: 354–361,1994; Nakayama, M. et al., Kidney Int., 51: 182–186,1997; Miyata, T. et al., Kidney Int., 58:425–435, 2000; Inagi R., et al., FEBS Lett., 463:260–264, 1999; Combet, S., et al., J. Am. Soc. Nephrol., 11:717–728, 2000). Thus, the carbonyl stress is also presumed to cause morphorgical changes in the peritoneum accompanied by functional (water-removing ability) impairment in dialysis patients. Therefore, a method to decrease the stress is needed in the art.

As a method for decreasing carbonyl stress in peritoneal dialysis patients, the present inventor has filed a patent (PCT/JP99/04521) relating to the use of carbonyl compound-trapping agents, such as aminoguanidine.

Biguanide agents, which have been used as therapeutic agents for diabetes mellitus, antimicrobial drugs, and antimalarial drugs, are known as compounds with a guanidine backbone. The biguanide agents have a basal backbone shown in formula (1), and contain a highly reactive imino group (=NH). Thus, the biguanide agents are expected to have a carbonyl compound-removing activity, like those of aminoguanidine. However, it has been believed that biguanide agents lack the glycation-suppressing effect because of the difference in three-dimensional structure between the two compounds ("New chemical therapy for diabetes mellitus" pp 22–31, 3. Biguanide Agents; S Tanaka, Medical Core (1997)).

(1)

DISCLOSURE OF THE INVENTION

The object of the present invention is to provide carbonyl stress-decreasing agents that are effective against the state of systemic carbonyl stress.

The present inventor searched for compounds that remove carbonyl compounds accumulated in blood and such. As described in the reference of prior art cited above, the biguanide agents have been believed to lack the glycation-suppressing activity. However, the present inventor found that the concentration of carbonyl compounds in a medium can be reduced by using a biguanide agent, such as phenformin, metformin, and buformin, and thus, completed the present invention. More specifically, the present invention relates to the following:

[1] a carbonyl stress-decreasing agent comprising a biguanide agent or pharmacologically acceptable salt thereof as an active ingredient;

[2] the carbonyl stress-decreasing agent of [1], wherein the biguanide agent is a compound selected from the group consisting of: phenformin, metformin, buformin, and pharmacologically acceptable salts thereof;

[3] a carrier, on which a biguanide agent has been immobilized;

[4] the carrier of [3], wherein the carrier is selected from the group consisting of: synthetic or naturally-occurring organic macro-molecular compounds; inorganic materials, such as glass beads, silica gel, alumina, and activated charcoal; and materials coated with polysaccharide(s) or synthetic polymer(s) thereof;

[5] the carrier of [3], wherein the shape of the carrier is selected from the group consisting of: membranous, fibrous, granular-shaped, hollow fiber-like, non-woven fabric-like, porous, and honeycomb-shaped carrier;

[6] the carrier of [3], wherein the carrier has a body fluid contact area that can be controlled by changing: thickness, surface area, diameter, length, shape, and/or size of the carrier:

[7] the carrier of [3], wherein the carrier is a hemodialysis membrane;

[8] the carrier of [3], wherein the biguanide agent is immobilized on the carrier by physical adsorption, a specific biochemical binding reaction, ion binding, covalent bonding, or grafting;

[9] an adsorbent of carbonyl compounds comprising any of the carriers of [3] to [8];

[10] a peritoneal dialysate solution comprising the carbonyl stress-decreasing agent of [1];

[11] a method for removing carbonyl compounds comprising the step of contacting the carrier of [3] with a body fluid selected from the group consisting of: blood, blood plasma and peritoneal dialysate;

[12] the method of [11] wherein the removal of the carbonyl compounds are carried out during in vivo or ex vivo blood purification step; and

[13] the method of [12], wherein the blood purification step comprises one or more steps selected from the group consisting of: hemodialysis, blood filtration, blood filtration dialysis, blood adsorption, and blood plasma separation.

Further, the present invention relates to the use of biguanide agents or pharmacologically acceptable salts thereof to produce the carbonyl stress-decreasing agents. The present invention also relates to the use of carriers, on which a biguanide agent has been immobilized, to produce carbonyl-compound adsorbents.

Biguanide agents are a group of compounds which have a guanidine backbone; they have been used as therapeutic agents for diabetes mellitus. Recently, biguanide agents have been widely used in place of sulfonyl urea (SU) agent, an agent that had been used as an oral antidiabetic drug for a long period. It has been reported that biguanides lack the activity to enhance insulin secretion, but have the activity of enhancing glycolysis to reduce blood glucose levels in living bodies. However, the interaction between biguanides and carbonyl compounds has not yet been reported, and thus, the finding of the present invention is entirely new.

As used herein, the term "biguanide agent" refers to, for example, a compound having the structure of formula (1) shown below. Wherein, R1, R2, R3, and R4 are independently selected from H, phenyl group, and alkyl group. The alkyl group includes phenetyl group, methyl group, butyl group, etc.

Formula (1):

Compounds with the above structure that act on carbonyl compounds causing carbonyl stress to inhibit the protein-modifying action thereof are used in the present invention.

Causative carbonyl compounds of carbonyl stress of the present invention include, for example, the following compounds that accumulate in blood of renal failure patients due to oxidative stress:

Carbonyl compounds derived from carbohydrates:
arabinose
glyoxal
methylglyoxal
3-deoxyglucosone.

Carbonyl compound derived from ascorbic acid:
dehydroascorbic acid.

Carbonyl compound derived from lipid:
hydroxynonenal
malondialdehyde
acrolein.

Further, during sterilization or storage of peritoneal dialysate, for example, the following carbonyl compounds are known to be produced in the peritoneal dialysate (Richard, J. U. et al., Fund. Appl. Toxic., 4: 843–853 (1984)). These carbonyl compounds, which are transferred through dialysis into the body of patients, are also pointed out as the cause of the carbonyl stress state in patients:

3-deoxyglucosone
5-hydroxymethylfurfural
formaldehyde
acetaldehyde
glyoxal
methylglyoxal
levulinic acid
furfural
arabinose.

A carbonyl stress-decreasing agent of the present invention comprises a biguanide agent as the active ingredient. As used herein, the term "decreasing carbonyl stress" refers to reducing the reactivity of carbonyl compounds in a medium which is contacted with living bodies, and thus, alleviating protein modification. Specifically, for example, when a compound has a potential for adsorbing or removing carbonyl compounds, or a potential for reducing the reactivity to amino groups, then the compound is assumed to have the activity of relieving carbonyl stress. The term "medium which is contacted with living bodies" specifically refers to peritoneal dialysate, blood, and other body fluids. Biguanide agents that can be used in the present invention include the following compounds, and pharmacologically acceptable salts thereof:

phenformin (phenethyl biguanide)

metformin (dimethyl biguanide)

buformin (butyl biguanide)

proguanil chlorhexidine

A carbonyl stress-decreasing agent of the present invention can be used in combination with compounds comprising, for example, the following compounds, or derivatives thereof, that function as a carbonyl compound-trapping agents. The term "derivatives" herein, refers to compounds having an atomic or molecular substitution(s) at any position of the parent compound.

(1) Guanidine derivatives, such as methylguanidine (JP-A Sho 62-142114; JP-A Sho 62-249908; JP-A Hei 1-56614; JP-A Hei 1-83059; JP-A Hei 2-156; JP-A Hei 2-765; JP-A Hei 2-42053; JP-A Hei 6-9380; and Published Japanese Translation of International Publication 5-505189);

(2) hydrazine derivatives, such as sulfonylhydrazine;

(3) five-membered heterocyclic compounds having two nitrogen atoms, such as pyrazolone (JP-A Hei 6-287179), pyrazoline (JP-A Hei 10-167965), pyrazole (JP-A Hei 6-192089; JP-A Hei 6-298737; and JP-A Hei 6-298738), imidazolidine (JP-A Hei 5-201993; JP-A Hei 6-135968; JP-A Hei 7-133264; and JP-A Hei 10-182460), and hydantoin (JP-A Hei 6-135968);

(4) five-membered heterocyclic compounds having three nitrogen atoms, such as triazole (JP-A Hei 6-192089);

(5) five-membered heterocyclic compounds having a nitrogen atom and a sulfur atom, such as thiazoline (JP-A Hei 10-167965), thiazole (JP-A Hei 4-9375; and JP-A Hei 9-59258), and thiazolidine (JP-A Hei 5-201993; JP-A Hei 3-261772; JP-A Hei 7-133264; and JP-A Hei 8-157473);

(6) five-membered heterocyclic compounds having a nitrogen atom and an oxygen atom, such as oxazole (JP-A Hei 9-59258);

(7) nitrogen-containing six-membered heterocyclic compounds, such as pyridine (JP-A Hei 10-158244; JP-A Hei 10-175954), and pyrimidine (Published Japanese Translation of International Publication 7-500811);

(8) nitrogen-containing condensed heterocyclic compounds, such as indazole (JP-A Hei 6-287180), and benzimidazole (JP-A Hei 6-305964) quinoline (JP-A Hei 3-161441);

(9) sulfur- and nitrogen-containing condensed heterocyclic compounds, such as benzothiazole (JP-A Hei 6-305964);

(10) sulfur-containing condensed heterocyclic compounds, such as benzothiophene (JP-A Hei 7-196498);

(11) oxygen-containing condensed heterocyclic compounds, such as benzopyran (JP-A Hei 3-204874; and JP-A Hei 4-308586);

(12) nitrogenous compounds, such as carbazoyl (JP-A Hei 2-156; and JP-A Hei 2-753), carbazic acid (JP-A Hei 2-167264), and hydrazine (JP-A Hei 3-148220);

(13) quinines, such as benzoquinone (JP-A Hei 9-315960), and hydroquinone (JP-A Hei 5-9114);

(14) aliphatic dicarboxylic acids (JP-A Hei 1-56614; and JP-A Hei 5-310565);

(15) silicone containing compounds (JP-A Sho 62-249709);

(16) organic germanium compounds (JP-A Hei 2-62885; JP-A Hei 5-255130; JP-A Hei 7-247296; and JP-A Hei 8-59485);

(17) flavonoids (JP-A Hei 3-240725; JP-A Hei 7-2,06838; JP-A Hei 9-241165; and WO 94/04520);

(18) alkylamines (JP-A Hei 6-206818; JP-A Hei 9-59233; JP-A Hei 9-40626; and JP-A Hei 9-124471);

(19) amino acids (Published Japanese Translation of International Publication 4-502611; and Published Japanese Translation of International Publication 7-503713);

(20) aromatic compounds, such as ascochlorin (JP-A Hei 6-305959), benzoic acid (WO 91/11997), and pyrrolo-naphthyridinium (JP-A Hei 10-158265);

(21) polypeptides (Published Japanese Translation of International Publication 7-500580);

(22) vitamins, such as pyridoxamine (WO 97/09981);

(23) SH group-containing compounds, such as glutathione, cysteine, and N-acetylcysteine;

(24) SH group-containing proteins, such as reduced albumin;

(25) tetracyclines (JP-A Hei 6-256280);

(26) chitosans (JP-A Hei 9-221427);

(27) tannins (JP-A Hei 9-40519);

(28) quaternary ammonium ion-containing compounds;

(29) ion exchange resins; and (30) inorganic compounds, such as activated carbon, silica gel, alumina, and calcium carbonate.

A carbonyl stress-decreasing agent of the present invention can be formulated in combination with physiologically acceptable carriers, excipients, diluents, and so on, to be administered orally or parenterally. Dosage forms for oral drug include glandules, powders, tablets, capsules, solutions, emersions, suspensions, etc.; and, those for parenteral drug include injections, drops, agents for external use, suppositories, and so on. The term "injection" encompasses intravenous injection, subcutaneous injection, intramuscular injection, intraperitoneal injection, and such. The agents for external use include intranasal drugs, adhesive skin patches, ointments, and so on. Such dosage forms with a biguanide agent as the base can be formulated by conventional methods.

For example, tablets for oral administration can be produced by combining biguanide agents with excipients, disintegrating agents, binding agents, lubricants, and such, to press-form the mixture. Typical excipients are exemplified by lactose, starch, mannitol, and the like. Calcium carbonate, calcium carboxymethyl cellulose, and such are generally used as disintegrating agents. Gum Arabic, carboxymethyl cellulose, polyvinylpyrrolidone, and such are typically used as binding agents. Known lubricants include talc, magnesium stearate, and so on.

A tablet containing a carbonyl stress-decreasing agent of the present invention can be coated for masking or for making into enteric-coated preparations according to conventional methods. Such coating agents include ethyl cellulose, polyoxyethyleneglycol, and so on.

An injection can be prepared by dissolving a biguanide agent as the base together with an appropriate dispersant, or dissolving or dispersing the agent in a dispersion medium. Depending on the type of the selected dispersion medium, the dosage form can be an aqueous solution or an oleaginous solution. Dispersion media used to prepare aqueous solutions includes distilled water, physiological saline, Ringers solution, and soon. Various vegetable oils, propyleneglycol, and the like can be exemplified as the dispersion media for preparing an oleaginous solution. Additionally, preservatives, such as paraben, can also be added according to needs. Further, known isotonizing agents, such as sodium chloride, and glucose; and pH-adjusting agents, such as hydrochloric acid, and sodium hydroxide, can be added to the injection. Furthermore, soothing agents, such as benzalkonium chloride, and procaine hydrochloride, can be added to the injection.

A carbonyl stress-decreasing agent of the present invention can be formulated for external use as a solid, liquid, or semi-solid composition comprising a biguanide agent. The solid or liquid composition for external use can be prepared according to the method mentioned above for preparing compositions. The semi-solid composition can be prepared by adding a thickening agent(s) to an appropriate solvent(s) according to needs. Such solvents include water, ethyl alcohol, polyethyleneglycol, and so on. Typical thickening agents include bentonite, polyvinyl alcohol, acrylic acid, methacrylic acid, polyvinylpyrrolidone, and so on. The composition may contain preservatives, such as benzalkonium chloride. Further, an agent of the present invention can also be formulated into a suppository by the combined use of an oily base, such as cacao butter, or an aqueous gel base, such as cellulose derivatives, as a carrier.

The biguanide agents, used as the base of the carbonyl stress-relieving agents of the present invention, are compounds that have been previously used as pharmaceuticals. Accordingly, required amounts of the agents, within a dose range ensuring the safety in usual cases, can be administered to mammals including human. The doses are properly selected depending on the type of administration method (dosage form), and condition of subject (size, age, sex, symptom, etc.). Generally, in the case of oral administration, a dose of typically 0.001 to 10 mg, more preferably 0.01 to 1 mg/day/kg body weight (human adult) is administered to gain a carbonyl stress-decreasing effect. The frequency of administration can be selected properly, for example, from a range of 1 to 5 times a day. No explicit toxicity is recognized for the biguanide agents of the present invention administered to decrease carbonyl stress.

A carbonyl stress-decreasing agent of the present invention can be administered to a living body by adding the agent to a peritoneal dialysate. Peritoneal dialysis is carried out by injecting a dialysate into peritoneal cavity; thus, a carbonyl stress-decreasing agent of the present invention can be administered by previously adding the agent into the peritoneal dialysate. The carbonyl compounds that exude into the peritoneal dialysate react with the biguanide agent to be detoxified, and, as a result, the carbonyl stress state is improved. Further, a biguanide agent previously added to the dialysate is expected to preventively detoxify the carbonyl compounds produced by various treatments of the dialysate, such as autoclaving during the process of production, and storage. A biguanide agent is added at a concentration of, for example, 0.5 to 100 mM, typically 1 to 50 mM, and preferably 5 to 20 mM to a peritoneal dialysate of the present invention.

A carbonyl stress-decreasing agent of the present invention can not only be directly administered to a living body, but also can be contacted with blood or dialysate outside the living body in methods for decreasing carbonyl stress. A biguanide agent is advantageously immobilized on a carrier for such methods.

There is no particular restriction on the carrier that is used for immobilizing a biguanide agent of the invention, so long as the carrier is harmless to human body, and is sufficiently safe and stable as a material to be directly contacted with blood or peritoneal dialysate. Such carriers include, for example, synthetic or naturally-occurring organic macromolecular compounds; inorganic materials, such as glass beads, silica gel, alumina, and activated charcoal; and materials coated with polysaccharide(s) or synthetic polymer(s) thereof.

A carrier consisting of macromolecular compounds is exemplified by polymethyl methacrylate polymer, polyacrylonitrile polymer, polysulfone polymer, vinyl polymer, polyolefin polymer, fluorine polymer, polyester polymer, polyamide polymer, polyimide polymer, polyurethane polymer, polyacryl polymer, polystyrene polymer, polyketone polymer, silicon polymer, cellulose polymer, and chitosan polymer. More specifically, carriers are exemplified by polysaccharides, such as agarose, cellulose, chitin, chitosan, sepharose, dextran, etc., and derivatives thereof; and polyester, polyvinyl chloride, polystyrene, polysulfone, polyethersulfone, polypropylene, polyvinyl alcohol, polyallylether sulfone, polyacrylic ester, polymethacrylic ester, polycarbonate, acetylated cellulose, polyacrylonitrile, polyethylene terephthalate, polyamide, silicone resin, fluororesin, polyurethane, polyetherurethane, and polyacrylamide, and derivatives thereof. The macromolecular materials can be used alone or in combination of two or more kinds of macromolecules. In the latter case, a biguanide agent is immobilized on at least one of the macromolecules. Further, a biguanide agent may be immobilized alone on a carrier, or two of more kinds of biguanide agents may be immobilized on the carrier.

There is no restriction on the shape of the carrier immobilizing the biguanide agent of the present invention. For example, the carrier can be membranous, fibrous, granular-shaped, hollow fiber-like, non-woven fabric-like, porous, honeycomb-shaped, and so on. The area of the carrier, to be contacted with blood or dialysate, can be controlled by changing the thickness, surface area, diameter, length, shape, and/or size of the carrier.

A biguanide agent can be immobilized on the above-mentioned carrier using conventional methods, such as physical adsorption, a specific biochemical binding reaction, ion binding, covalent bonding, grafting, and so on. According to needs, spacers can be inserted between carrier and biguanide agent. Preferably, a carrier and a biguanide agent are bound by covalent bonds so as to minimize the amount of the biguanide agent released. Functional groups on the carrier are utilized for covalently binding a biguanide agent thereto. The functional groups include, for example, hydroxyl group, amino group, aldehyde group, carboxyl group, thioli group, silanol group, amide group, epoxy group, succinylimido group, and so on; however, the functional groups of the present invention are not limited to these groups. The covalent bonds are exemplified by ester linkage, ether linkage, amino linkage, amid linkage, sulfide linkage, imino linkage, disulfide linkage, and so on.

The carrier with a biguanide agent of the present invention immobilized on it can be sterilized by conventional sterilization methods. Specifically, sterilizationmethods includes, for example, autoclaving, gamma-ray irradiation, gas sterilization, and so on.

Biguanide agent-immobilized carriers can be contacted with blood in various ways. Examples thereof include: a method of trapping carbonyl compounds in patient blood by infusing the blood collected from the patient into a blood bag filled with biguanide agent-immobilized carriers; a method where blood is circulated in a cartridge column filled with bead carriers or fiber carriers, or the like, on which a biguanide agent has been immobilized; and so on. Instead of whole blood, blood plasma separated therefrom may be also treated according to the method. The treated blood may be returned to the patient or, if required, may be stored in a blood bag, or the like. Carbonyl compounds that generate and/or accumulate during storage can be also trapped by adding carriers immobilized with biguanide agents into the blood bags.

The contact between blood and carriers, on which a biguanide agent of this invention has been immobilized, can be carried out during the blood purification step, including hemodialysis., blood filtration, blood filtration dialysis, blood adsorption, and blood plasma separation.

For example, both hemodialysis and trapping of carbonyl compounds can be carried out simultaneously in hemodialysis patients by placing carriers on which a biguanide agent has been immobilized in the hemodialysis circuit. Herein, a biguanide agent is preferably immobilized on the hemodialysis membrane. Known types of dialysis membranes can be used as carriers. Examples include: cellulose derivatives, such as regenerated cellulose, and cellulose triacetate; polymethyl methacrylate; polyolefin; polysulfone; polyacrylonitrile (PAN); polyamide; polyimide; polyether nylon; silicon; polyester copolymers; and so on; however, the present invention is not limited thereto. Instead of using a dialysis membrane as a carrier, a column filled with carriers, on which a biguanide agent has been immobilized, may be placed in the hemodialysis circuit as described above. By contacting patient's blood with carriers, on which a biguanide agent has been immobilized, carbonyl compounds are trapped from the blood, and the damaging activity of the compounds against the living body are eliminated and rendered nontoxic. Anticoagulants may be combined to prevent blood-clotting during extracorporeal circulation. Such anticoagulants include, for example, heparin, low-molecular-weight heparin, Futhan (Nafamostat mesilate), and so on. They may also be immobilized on carriers.

A method wherein peritoneal dialysate, instead of blood, is contacted with an immobilized biguanide agent is also useful to improve the carbonyl stress state. For example, carbonyl compounds generated and/or accumulated during storage can be trapped by enclosing the peritoneal dialysate in a container wherein a biguanide agent is immobilized therein; or in a container comprising a biguanide agent immobilized on particulates or fibrous carriers. In the latter system, the insoluble carriers can be separated from the peritoneal dialysate by filtration and the like. Alternatively, a carbonyl compound-trapping cartridge is prepared by filling a column with carrier beads or fibrous carriers, on which a biguanide agent is immobilized. Then, peritoneal dialysate is contacted with the carrier in the cartridge, and then, the fluid is infused into peritoneal cavity. When the carbonyl compound-trapping cartridge is contacted with peritoneal dialysate at the time of peritoneal infusion, although it is impossible to remove patient-derived carbonyl compounds that accumulate in the fluid during the dialysis, carbonyl compounds originally present in the dialysate can be eliminated. Alternatively, when peritoneal dialysis treatment is conducted by using a closed circuit, wherein peritoneal dialysate is circulated by a small circulating pump, it is possible to remove not only carbonyl compounds originally present in the dialysate but also those that accumulate in the peritoneal cavity during dialysis by installing the above-mentioned carbonyl compound-trapping cartridge containing carriers with immobilized biguanide agent within the circuit.

It is predicted that there may be some cases where carbonyl compounds in patient blood are not completely eliminated during dialysis if the quantity of biguanide agent used for the contact with blood or dialysate is too small. Pre-determination of the quantity of carbonyl compounds in patient blood is particularly difficult. Thus, to be most effective, it is preferable to maintain as many biguanide agents as active as possible, within a range that ensures the safety of the patient. The dose of a biguanide agent can be adjusted by altering the quantity of biguanide agent immobilized on the carriers, or the dose of carriers on which the biguanide agent has been immobilized.

The effect of a carbonyl stress-decreasing agent of the present invention can be confirmed by monitoring the concentration of carbonyl compounds or AGE in blood. The in vivo effect can be assessed by comparing blood AGE levels between a control group and a group wherein a carbonyl stress-decreasing agent of the present invention has been administered. The control group may be an untreated group or a group wherein physiological saline or a control agent, consisting of the decreasing agent without the base agent, i.e. biguanide agent, has been administered. Glyoxal (GO), methylglyoxal (MGO), and 3-deoxyglucosone (3DG) can be used as indices of carbonyl compounds. The levels of these carbonyl compounds can be readily determined by HPLC or the like as shown in the Examples (Ohmori S. et al., J. Chromatogr. 414:149–155, 1987; Yamada H., J. Biol. Chem. 269:20275–20280, 1994). Alternatively, the levels of the carbonyl compounds can be determined by reacting them with 2,4-dinitrophenylhydrazine (2,4-DNPH) under an acidic condition, and measuring the optical density of colored products of the reaction at 360 nm. Further, pentosidine or the like can be used as an index of AGE. A method for quaritifying pentosidine with reverse-phase HPLC is already known in the art (Miyata T, et al., J Am Soc Nephrol 7: 1198–1206, 1996).

Generally, orally administered biguanide agents exhibit the maximal blood level 1 to 2 hours after administration (N. Engl. J. Med. 334:574–579, 1996). Accordingly, the effect of a decreasing agent of the present invention can be tested by monitoring changes of pentosidine level during this period. The effect of a decreasing agent of the invention can be assessed by decreased pentosidine levels compared with the level of a control. On the other hand, the concentration of carbonyl-compounds and AGE in blood or dialysate is detected to assess the effect of a carbonyl stress-decreasing agent of the present invention outside the living body.

BEST MODE FOR CARRYING OUT THE INVENTION

The present invention is illustrated in detail below with reference to Examples.

EXAMPLE 1

Carbonyl Compound-Trapping Effect of Biguanide Agents

100 μl of a mixed solution of representative carbonyl compounds, i.e. glyoxal (GO), methylglyoxal (MGO), and 3-deoxyglucosone (3DG) (1 mM each), was combined with 800 μl of 0.1M phosphate buffer (pH7.4) and 100 μl of 30 mM biguanide agent solution, and was incubated at 37° C. Metformin, buformin, and phenformin were used as biguanide agents. After the incubation, the concentrations of glyoxal, methylglyoxal, and 3-deoxyglucosone in the solution were determined by high-performance liquid chromatography. More specifically, 40 μl of 2M perchloric acid, 40 μl of 1% o-phenylenediamine, 100 μl of 50 μM 2,3-butanedione were added to 100 μl of the sample after the incubation; the mixture was stirred and incubated at 25° C. for 1 hour. Quinoxaline derivatives, which are products of the reaction between dicarbonyl compounds and o-phenylenediainine, were quantified by HPLC using a reverse-phase column according to the method of Ohmori et al. (Ohmori S. et al., J. Chromatogr. 414:149–155, 1987). Glyoxal, methylglyoxal, and 3-deoxyglucosone were used as standard samples.

Figure 1:
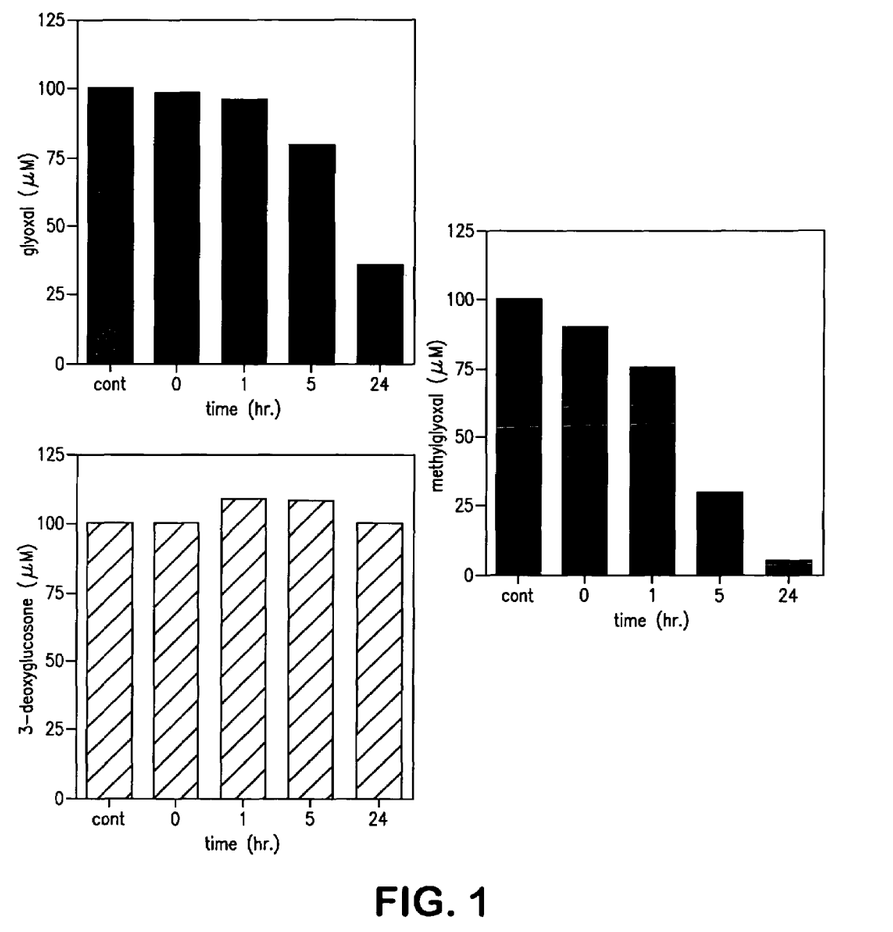
FIG. 1 depicts graphs demonstrating the carbonyl compound-trapping effect of a biguanide agent (metformin). The ordinate-indicates the concentration of the carbonyl compound (μM) determined by high-performance liquid chromatography; the abscissa indicates the incubation time (hr.).
Figure 2:
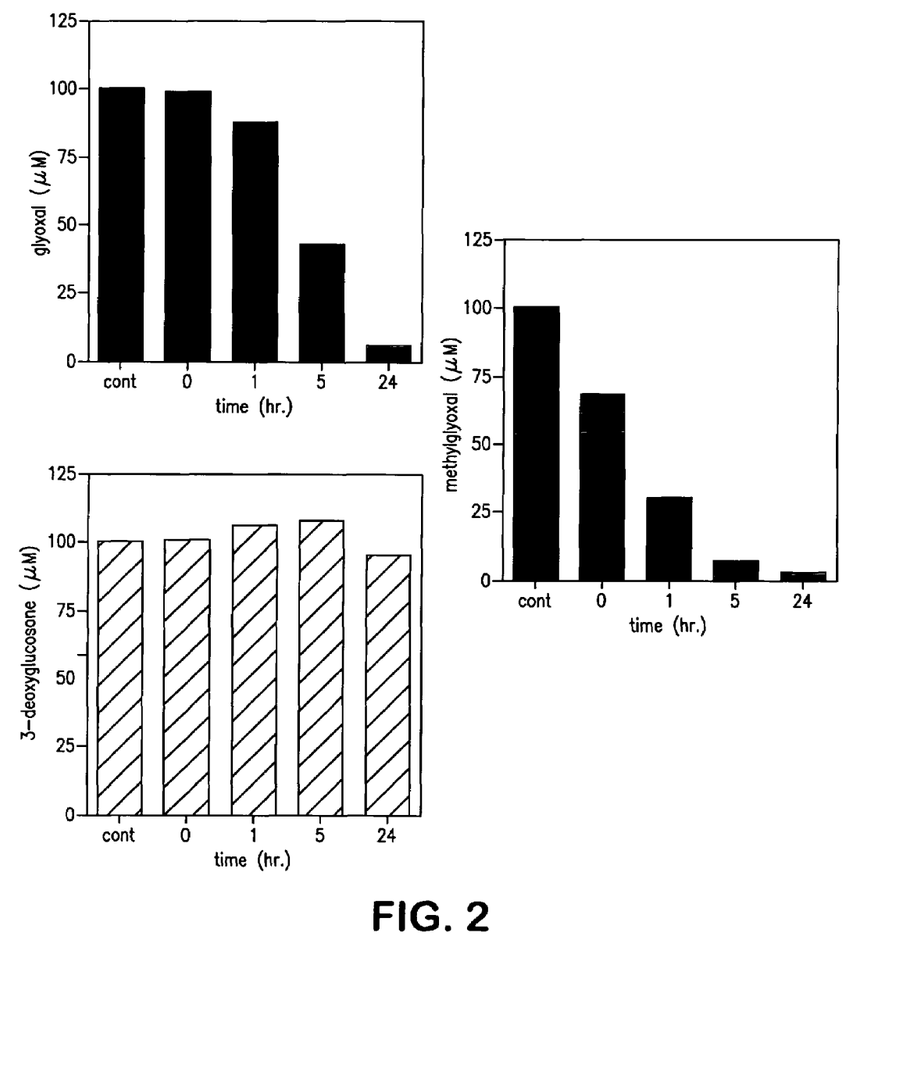
FIG. 2 depicts graphs demonstrating the carbonyl compound-trapping effect of a biguanide agent (buformin). The ordinate indicates the concentration of the carbonyl compound (μM) determined by high-performance liquid chromatography; the abscissa indicates the incubation time (hr.).
Figure 3:
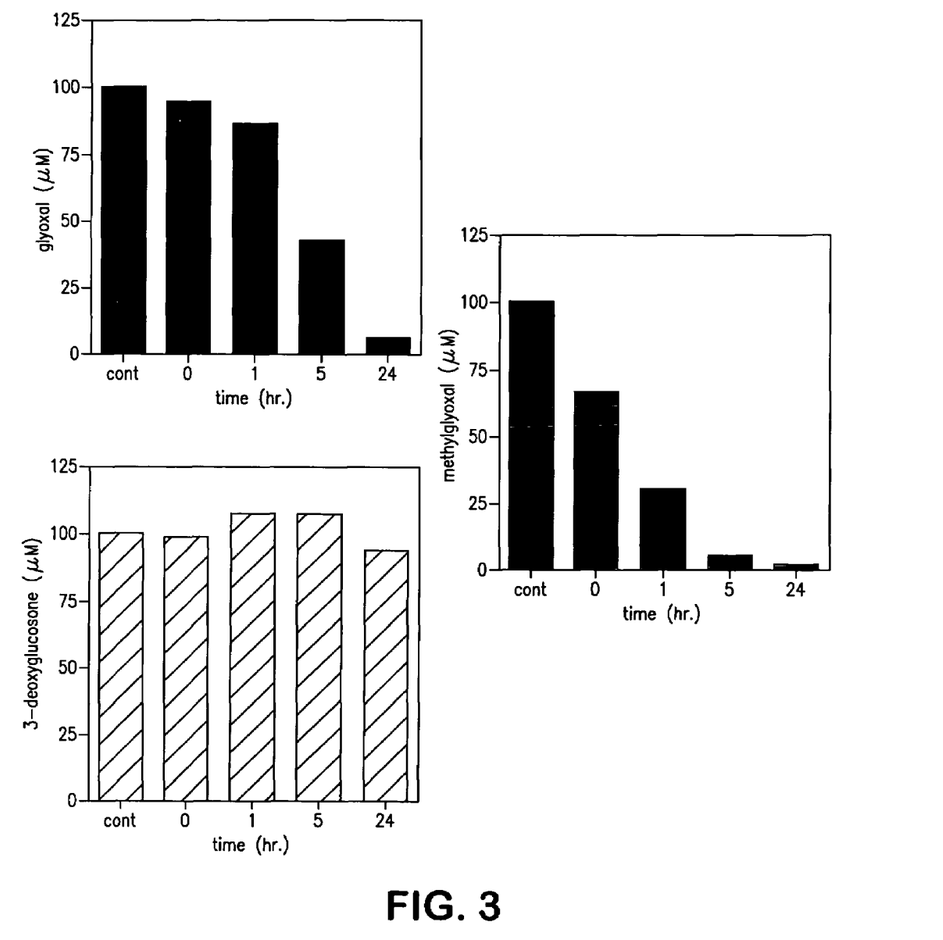
FIG. 3 depicts graphs demonstrating the carbonyl compound-trapping effect of a biguanide agent (phenformin). The ordinate indicates the concentration of the carbonyl compound (μM) determined by high-performance liquid chromatography; the abscissa indicates the incubation time (hr.).
Figure 4:
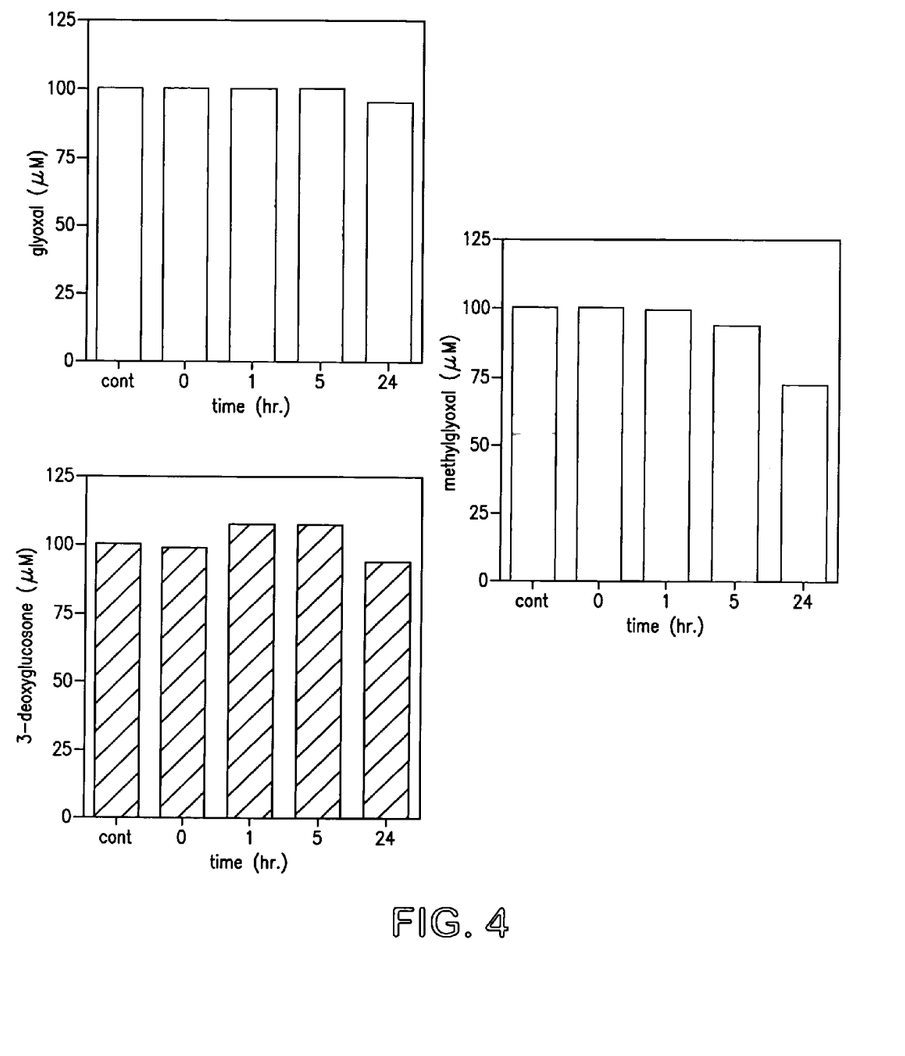
FIG. 4 depicts graphs demonstrating the changes of concentration of carbonyl compounds, which was determined in the absence of any biguanide agent (control). The ordinate indicates the concentration of the carbonyl compound (μM) determined by high-performance liquid chromatography; the abscissa indicates the incubation time (hr.).

The results are shown in FIG. 1 (metformin), FIG. 2 (buformin), and FIG. 3 (phenformin). Almost no change in the carbonyl compound levels during the incubation is observed with the carbonyl compounds alone (FIG. 4; control). On the other hand, in the presence of a biguanide agent selected from those mentioned above, the concentrations of glyoxal and methylglyoxal were markedly decreased depending on the incubation period by each agent, and the carbonyl compound-trapping effect of the biguanide agents was confirmed. Thus, the carbonyl compounds were verified to lose their reactivity by reacting with the biguanide agents.

EXAMPLE 2

Dicarbonyl-Trapping Action of Biguanide Agents in Peritoneal Dialysates

Peritoneal dialysates comprise carbonyl compounds generated during autoclaving or storage. The carbonyl compounds, which are generated during the processes of production or storage of the peritoneal dialysate, can be preventively detoxified by previously adding a biguanide agent to the peritoneal dialysate. Alternatively, the carbonyl compounds can be removed by contacting the peritoneal dialysate with a carrier immobilized with the biguanide agent.

First, the quantities of various carbonyl compounds in a commercially available peritoneal dialysate (Baxter Ltd.; Dianeal PD-4 1.5™) were determined according to the method of Ohmori et al. (Ohmori S. et al., J. Chromatogr., 414:149–155, 1987). The concentrations of glyoxal, methylglyoxal, and 3-deoxyglucosone in the peritoneal dialysate were determined to be 11 µM, 3.5 µM, and 42 µM, respectively.

Then, 100 µl of a biguanide solution (dissolved in 0.1M phosphate buffer (pH 7.4)) was added to 900 µL of the peritoneal dialysate (Baxter Ltd.; Dianeal PD-4 1.5™) to prepared a sample solution. The final concentrations of the biguanide agents were adjusted to 0, 1, 5, and 10 mM. Metformin, buformin, and phenformin were used as biguanide agents. The mixed sample solution was incubated at 37° C. for 4 hours.

The quantities of residual glyoxal, methylglyoxal, and 3-deoxyglucosone in the sample solution were determined by high-performance liquid chromatography (HPLC) following the incubation. More specifically, 40 µl of 2M perchloric acid, 40 µl of 1% o-phenylenediamine, and 100 µl of 25 µM 2,3-butanedione were added to 100 µl of the sample after the incubation; the mixture was stirred and incubated at 25° C. for 1 hour. Quinoxaline derivatives produced in the reaction of the dicarbonyl compounds and o-phenylenediamine were quantified by HPLC using a reverse-phase column according to the method of Ohmori et al. (Ohmori S. et al., J. Chromatogr. 414: 149–155,1987). Glyoxal, methylglyoxal, and 3-deoxyglucosone were used as standard samples.

Figure 5:
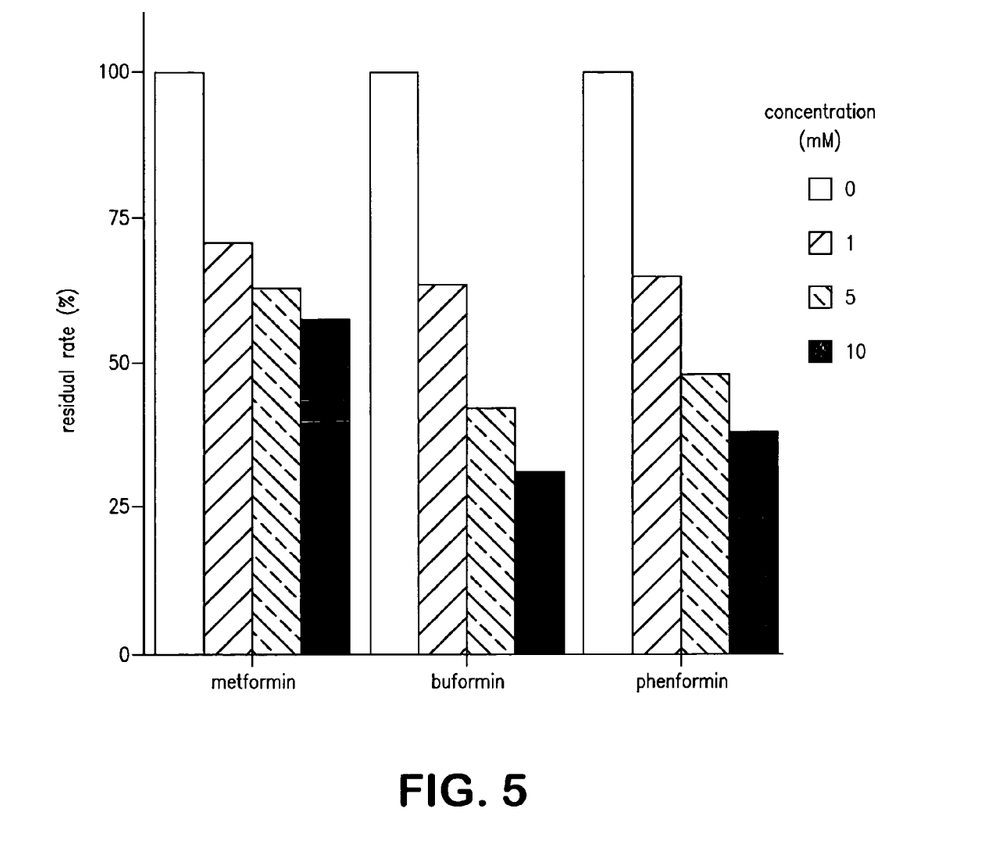
FIG. 5 depicts a graph demonstrating the dicarbonyl compound (glyoxal)-trapping action of biguanide agents in peritoneal dialysate. The ordinate indicates the residual rate (%) of glyoxal in the peritoneal dialysate; the abscissa indicates the type of the biguanide agent.
Figure 6:
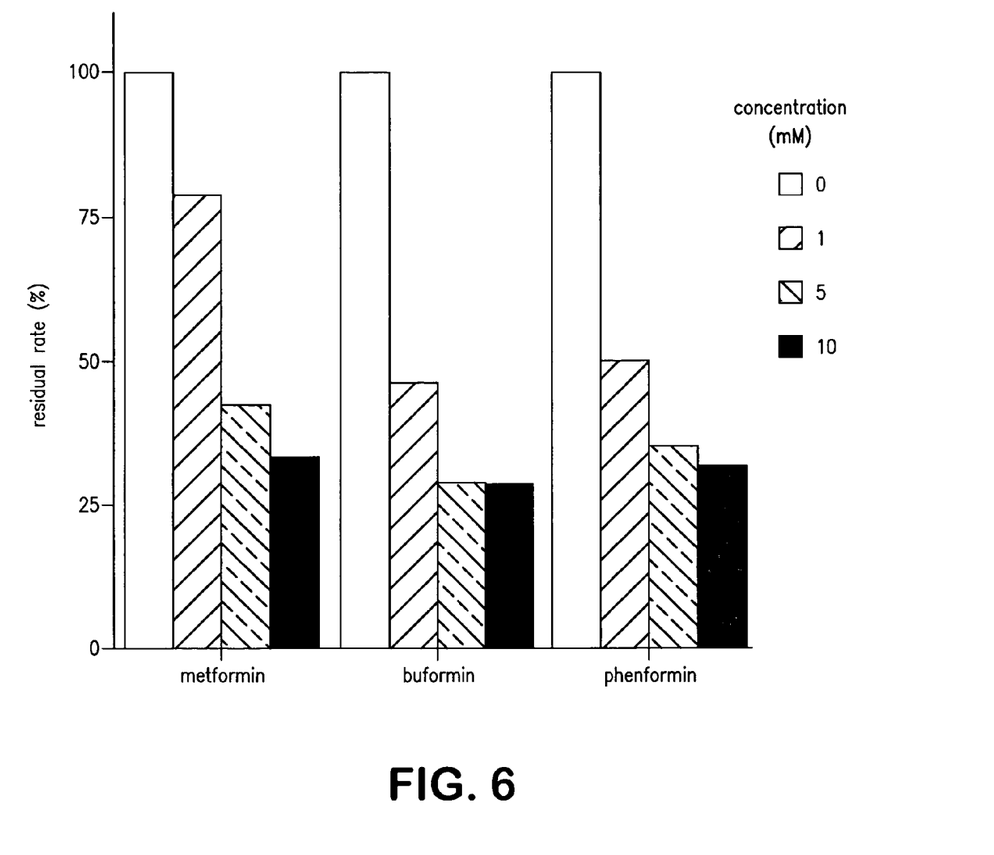
FIG. 6 depicts a graph demonstrating the dicarbonyl compound (methylglyoxal)-trapping action of biguanide agents in peritoneal dialysate. The ordinate indicates the residual rate (%) of methylglyoxal in the peritoneal dialysate; the abscissa indicates the type of the biguanide agent.
Figure 7:
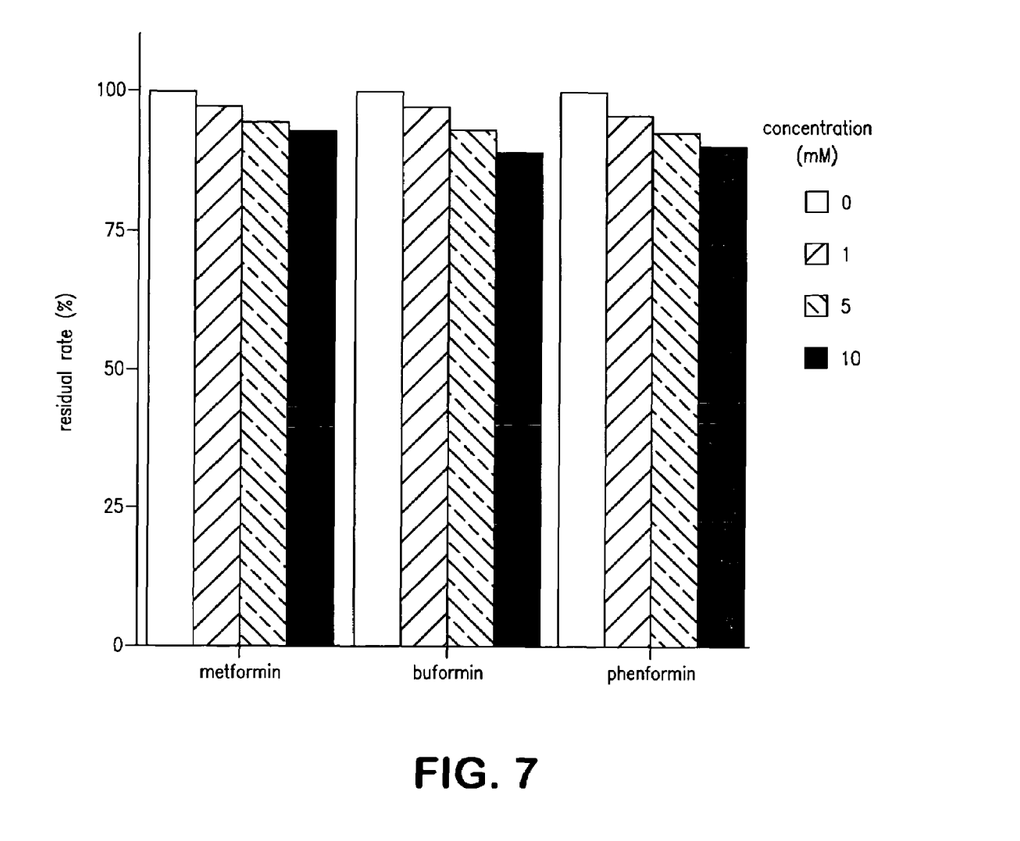
FIG. 7 depicts a graph demonstrating the dicarbonyl compound (3-deoxyglucosone)-trapping action of biguanide agents in peritoneal dialysate. The ordinate indicates the residual rate (%) of 3-deoxyglucosone in the peritoneal dialysate; the abscissa indicates the type of the biguanide agent.

The results are shown in FIG. 5 (glyoxal), FIG. 6 (methylglyoxal), and FIG. 7 (3-deoxyglucosone). The quantity of each carbonyl compound is represented by the residual rate (%), taking the quantity in the absence of any biguanide agent as 100%. In the presence of a biguanide agent, the concentrations of glyoxal and methylglyoxal were decreased depending on the biguanide concentration, and thus, the dicarbonyl compound-trapping effect in a peritoneal dialysate was confirmed.

EXAMPLE 3

Dicarbonyl-Trapping Action of a Biguanide Agent in Peritoneal Dialysis Effluent

During peritoneal dialysis, highly reactive carbonyl compounds, along with circulating waste products, are transferred across the peritoneum and accumulated in peritoneal dialysate in the patient's peritoneal cavity. Therefore, in order to study the ability of a biguanide agent to trap carbonyl compounds in peritoneal dialysate in peritoneal cavity during peritoneal dialysis, experiments were carried out to determine the effect of a biguanide agent to trap dicarbonyl compounds in peritoneal dialysis discharged from peritoneal cavity of a peritoneal dialysis patient.

First, 100 µl of biguanide solution (dissolved in 0.1M phosphate buffer (pH 7.4)) was added to 900 µl of peritoneal dialysis effluent (liquid allowed to dwell in the peritoneal cavity for 2 hours) from a peritoneal dialysis patient administered with a commercially available peritoneal dialysate (Baxter Ltd.; Dianeal PD-4 1.5™); the final concentrations of the biguanides were 0, 5, 25, and 50 mM. The mixture was incubated at 37° C. for 4 hours. Metformin, buformin, and phenformin were used as biguanide agents. After the incubation, 200 µl of water and 100 µl of 2M perchloric acid were added to 200 µl of the sample. The mixture was centrifuged and filtered with a 0.45-µm filter. 50 µl of 10 µM 2,3-butanedione and 20 µl of 1% O-phenylenediamine were added to 150 µl of the filtrate. The mixture was stirred and incubated at room temperature for 2 hours. Then, 40 µl of 5N sodium hydroxide solution was added, and the mixture was stirred. 600 µl of toluene was added to the mixture for extraction. Further, 2M perchloric acid was added to 500 µl of the toluene phase, and the mixture was stirred to extract quinoxaline derivatives. To quantify glyoxal and methylglyoxal, the aqueous phase was analyzed by HPLC using a reverse-phase column according to the method of Ohmori et al. (Ohmori S. et al., J. Chromatogr. 414: 149–155,1987). Glyoxal and methylglyoxal were used as standard samples.

Figure 8:
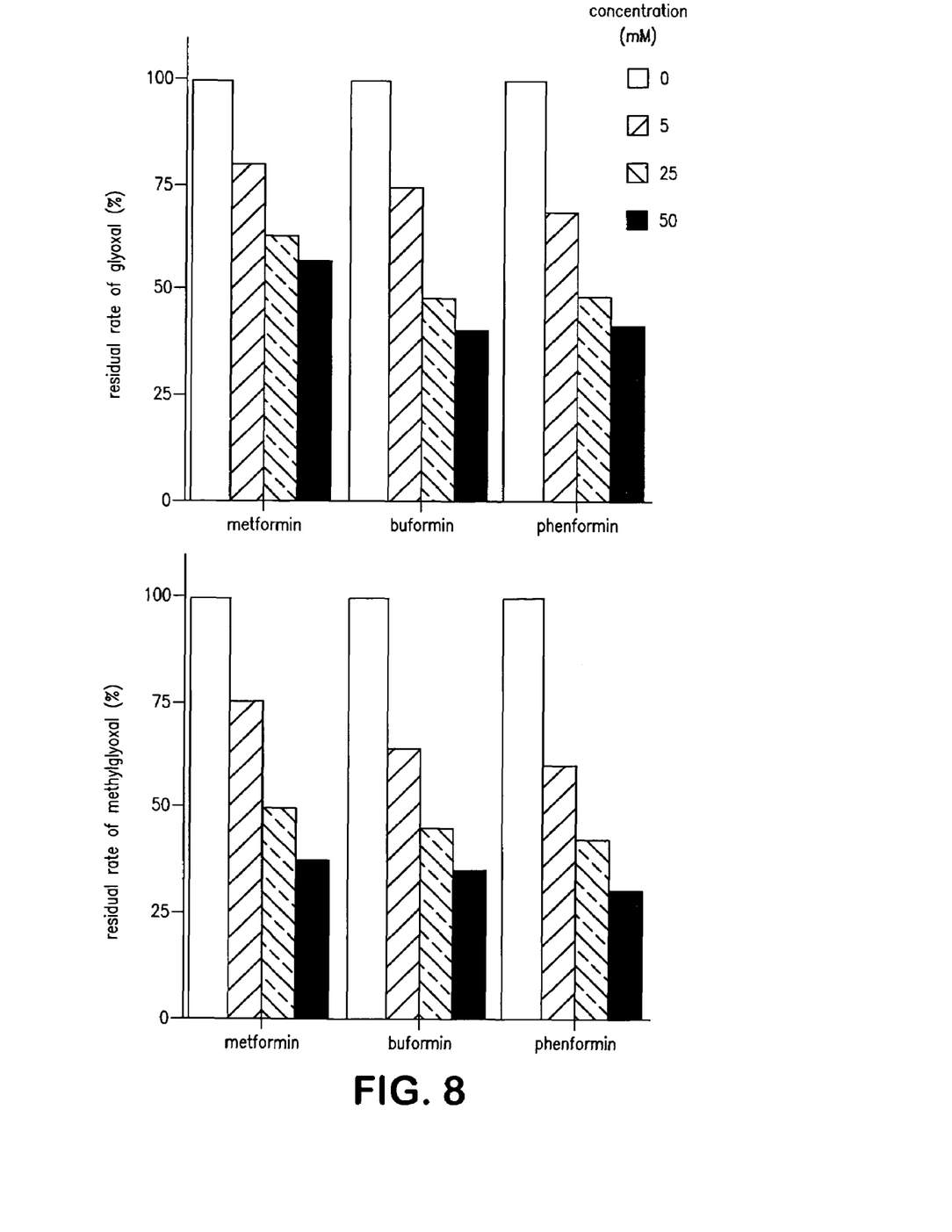
FIG. 8 depicts graphs demonstrating the dicarbonyl compound (glyoxal and methylglyoxal)-trapping action of biguanide agents in peritoneal dialysis effluent. The ordinate indicates the residual rates (%) of glyoxal and methylglyoxal in the peritoneal dialysis effluent; the abscissa indicates the type and the concentration of the biguanide agent.

The results are shown in FIG. 8. The quantity of each carbonyl compound is represented by the residual rate (%), taking the quantity in the absence of any biguanide agent as 100%. In the presence of a biguanide agent, the concentrations of glyoxal and methylglyoxal decreased, depending on the biguanide concentration, and thus, the dicarbonyl compound-trapping effect in a peritoneal dialysis effluent was confirmed.

EXAMPLE 4

The Action of a Biguanide Agent to Trap Dicarbonyl Compounds in Serum

In order to study the effect of the carbonyl stress-decreasing agents of the present invention in patients treated with blood dialysis, the action of biguanide agents to trap dicarbonyl compounds in serum was examined.

First, 100 µl of biguanide solution (dissolved in 0.1M phosphate buffer (pH 7.4)) was added to 900 µl serum from a blood dialysis patient; the final concentrations of the biguanides were 0, 5, 25, and 50 mM. The mixture was incubated at 37° C. for 4 hours. Metformin, buformin, and phenformin were used as biguanide agents. Glyoxal and methylglyoxal were quantified by the same method as in Example 3.

Figure 9:
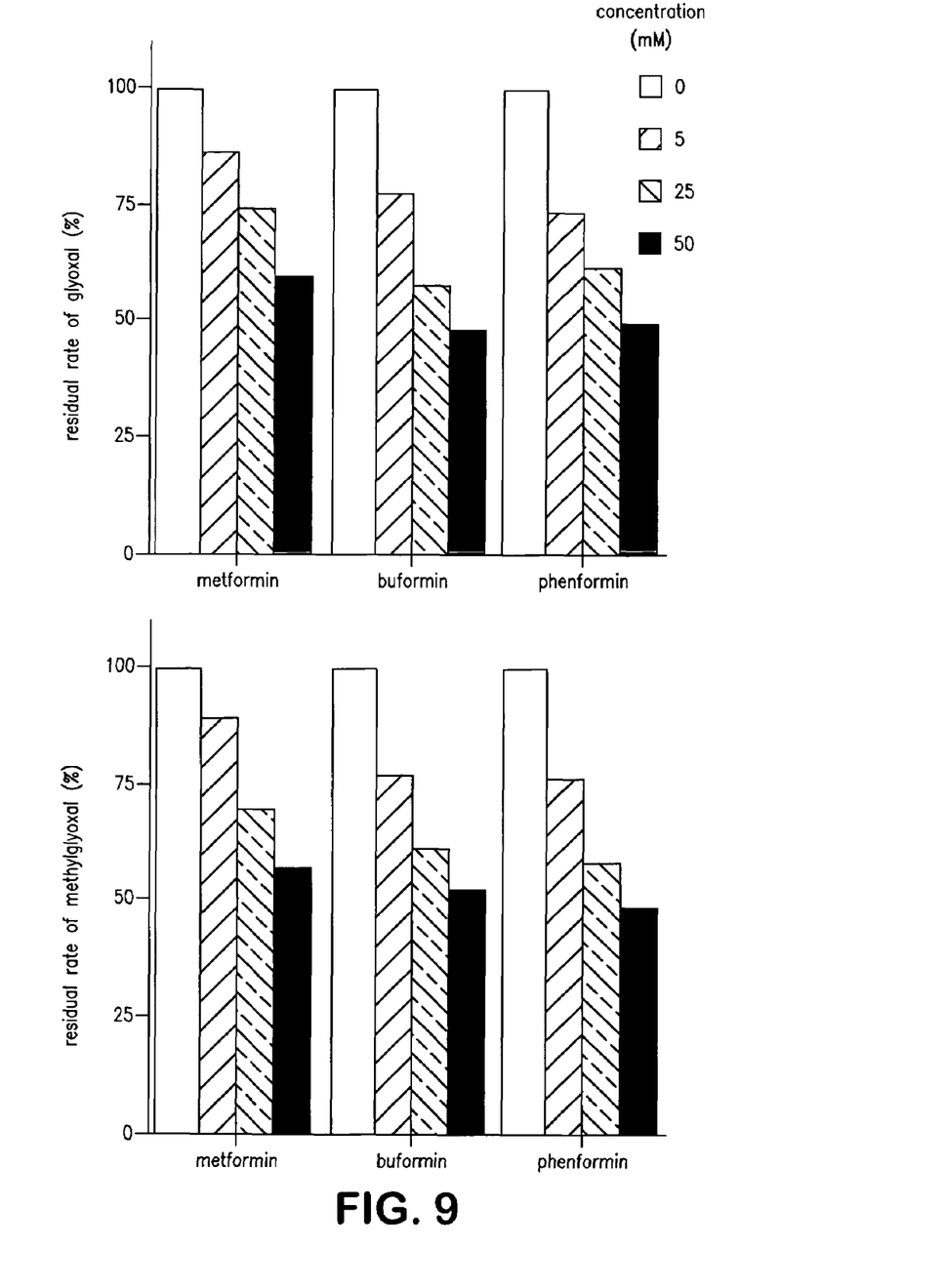
FIG. 9 depicts graphs demonstrating the dicarbonyl compound (glyoxal and methylglyoxal)-trapping action of biguanide agents in serum. The ordinate indicates the residual rates (%) of glyoxal and methylglyoxal in the serum; the abscissa indicates the type and the concentration of the biguanide agent.

The results are shown in FIG. 9. The quantity of each carbonyl compound is represented by the residual rate (%), taking the quantity in the absence of any biguanide agent as 100%. In the presence of a biguanide agent, the concentrations of glyoxal and methylglyoxal decreased, and thus, the dicarbonyl compound-trapping effect in serum was confirmed.

INDUSTRIAL APPLICABILITY

The present invention provides carbonyl stress-decreasing agents that are expected to remove carbonyl compounds both within a living body (in vivo) and outside the body (ex vivo). Biguanide agents constituting the carbonyl stress-decreasing agents of the present invention are oral antidiabetic drugs that have been used clinically, and therefore can be administered orally or by other routes for administration. The biguanide agents can be used as agents having direct action against in vivo carbonyl stress. Furthermore, the agents can be provided conveniently due to highly sophisticated formulation techniques previously established for the agents.

The invention claimed is:

1. A method of removing glyoxal and/or methylglyoxal from one or more body fluids selected from the group consisting of blood, blood plasma and peritoneal dialysate, the method comprising contacting a carrier on which one or more biguanide agents have been immobilized with said body fluids, thereby removing glyoxal and/or methylglyoxal in said body fluids, wherein the biguanide agents are selected from the group consisting of phenformin, buformin, and pharmacologically acceptable salts thereof.

2. The method of claim 1, wherein removing of glyoxal and/or methylglyoxal is carried out during in vivo or ex vivo blood purification.

3. A method of removing glyoxal and/or methylglyoxal from one or more body fluids selected from the group consisting of blood, blood plasma and peritoneal dialysate, the method comprising contacting one or more biguanide agents with said body fluids, thereby glyoxal and/or methylglyoxal in said body fluids are removed, wherein the biguanide agents are selected from the group consisting of phenformin, buformin, and pharmacologically acceptable salts thereof.

4. The method of claim 3, wherein removing of glyoxal and/or methylglyoxal is carried out during in vivo or ex vivo blood purification.

5. The method of claim 3, wherein the biguanide agent is orally administered.

6. The method of claim 3, wherein the biguanide agent is administered by injection.

7. The method of claim 1, wherein the carrier is one or more materials selected from the group consisting of synthetic or naturally-occurring organic macro-molecular compounds, inorganic material and materials coated with polysaccharide(s) and synthetic polymer(s) thereof.

8. The method of claim 1, wherein the carrier is an inorganic material.

9. The method of claim 8, wherein the inorganic materials are selected from the group consisting of glass beads, silica gel, alumina and activated charcoal.

10. The method of claim 8, wherein the carrier is a synthetic organic macro-molecular compound.

11. The method of claim 1, wherein the carrier is selected from the group consisting of a membranous, a fibrous, a granular-shaped, a hollow fiber-like, a non-woven fabric-like, a porous, and a honeycomb-shaped carrier.

12. The method of claim 1, wherein the carrier has a body fluid contact area that can be controlled by altering one or more parameters selected from the group consisting of thickness, surface area, diameter, length, shape and size of the carrier.

13. The method of claim 1, wherein the biguanide agent is immobilized on the carrier by one or more reactions selected from the group consisting of physical adsorption, a specific biochemical binding reaction, ion binding, covalent bonding and grafting.

14. The method of claim 1, wherein the carrier is a hemodialysis membrane.

15. The method of claim 2, wherein the blood purification comprises one or more steps selected from the group consisting of blood filtration, blood filtration dialysis, blood adsorption, and blood plasma separation.

16. The method of claim 4, wherein the blood purification comprises one or more steps selected from the group consisting of blood filtration, blood filtration dialysis, blood adsorption, and blood plasma separation.

* * * * *